(12) United States Patent
Huang et al.

(10) Patent No.: US 6,881,317 B2
(45) Date of Patent: Apr. 19, 2005

(54) FRACTIONATION OF MACRO-MOLECULES USING ASYMMETRIC PULSED FIELD ELECTROPHORESIS

(75) Inventors: Lotien Richard Huang, Princeton, NJ (US); James Christopher Sturm, Princeton, NJ (US); Robert Hamilton Austin, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 21 days.

(21) Appl. No.: 10/022,189

(22) Filed: Dec. 18, 2001

(65) Prior Publication Data

US 2002/0098504 A1 Jul. 25, 2002

Related U.S. Application Data

(60) Provisional application No. 60/256,298, filed on Dec. 18, 2000.

(51) Int. Cl.[7] .......................... C02F 1/40; C02F 11/00; C25B 11/00; G01N 15/06; G01N 1/00
(52) U.S. Cl. .................... 204/608; 422/50; 422/52; 422/58; 422/63; 422/68.1; 422/81; 422/82; 422/82.05; 422/82.08; 422/82.09; 422/100; 422/102; 422/103; 422/104; 436/8; 436/43; 436/174; 204/600; 204/601; 204/450; 204/451; 204/458; 700/1; 700/266; 700/273
(58) Field of Search .................... 422/50, 52, 58, 422/63, 68.1, 81, 82, 82.05, 82.08, 82.09, 100, 102, 103, 104; 436/8, 43, 174; 204/600, 601, 608, 450, 451, 458; 700/1, 266, 273

(56) References Cited

U.S. PATENT DOCUMENTS

| | | | |
|---|---|---|---|
| 4,473,452 A | 9/1984 | Cantor et al. | 204/180 |
| 4,523,320 A | 6/1985 | Stappaerts | 372/87 |
| 4,693,804 A | 9/1987 | Serwer | 204/182.1 |
| 4,737,251 A | 4/1988 | Carle et al. | 204/182.8 |
| 4,740,283 A | 4/1988 | Laas et al. | 204/182.8 |
| 4,830,726 A * | 5/1989 | Stamato et al. | 204/458 |
| 5,011,586 A | 4/1991 | Finney et al. | 204/299 |
| 5,106,468 A | 4/1992 | Chimenti | 204/180.1 |
| 5,116,471 A | 5/1992 | Chien et al. | 204/180.1 |
| 5,122,248 A | 6/1992 | Karger et al. | 204/182.8 |
| 5,178,737 A | 1/1993 | Lai | 204/182.8 |
| 5,405,519 A | 4/1995 | Schwartz | 204/299 R |
| 5,427,663 A | 6/1995 | Austin et al. | 204/180.1 |
| 5,972,190 A | 10/1999 | Richman | 204/600 |
| 6,027,623 A * | 2/2000 | Ohkawa | 204/450 |
| 6,110,339 A * | 8/2000 | Yager et al. | 204/451 |
| 6,156,273 A | 12/2000 | Regnier et al. | 422/70 |
| 6,176,990 B1 * | 1/2001 | Yager et al. | 204/601 |
| 6,254,754 B1 | 7/2001 | Ross et al. | 204/548 |
| 6,280,590 B1 | 8/2001 | Cheng et al. | 204/463 |
| 6,596,144 B1 * | 7/2003 | Regnier et al. | 204/601 |

FOREIGN PATENT DOCUMENTS

EP 0560974 B1 1/1997

* cited by examiner

Primary Examiner—Jill Warden
Assistant Examiner—Brian Sines
(74) Attorney, Agent, or Firm—McCarter & English, LLP

(57) ABSTRACT

A method and apparatus for fractionation of charged macro-molecules such as DNA is provided. DNA solution is loaded into a matrix including an array of obstacles. An alternating electric field having two different fields at different orientations is applied. The alternating electric field is asymmetric in that one field is stronger in duration or intensity than the other field, or is otherwise asymmetric. The DNA molecules are thereby fractionated according to site and are driven to a far side of the matrix where the fractionated DNA is recovered. The fractionating electric field can be used to load and recover the DNA to operate the process continuously.

45 Claims, 6 Drawing Sheets

FRACTIONATION OF MACRO-MOLECULES USING ASYMMETRIC PULSED FIELD ELECTROPHORESIS

RELATED APPLICATIONS

This application claims the priority of Provisional Application Ser. No. 60/256,298, filed Dec. 18, 2000, the entire disclosure of which is expressly incorporated herein by reference.

GOVERNMENT RIGHTS

The present invention has been made under Federal Contract Grant No. MDA 972-00-10031 and the government may have certain rights to the subject invention.

BACKGROUND OF THE INVENTION

1. Field of the Invention

The present invention relates to a method and apparatus for fractionating charged macro-molecules such as DNA using asymmetric pulsed field electrophoresis.

2. Related Art

The analysis and fractionation of large DNA molecules is a central step in large scale sequencing projects. Conventionally, gel electrophoresis is used to fractionate DNA molecules according to their sizes. This method includes two steps: sample loading and fractionation. First, sample solution containing DNA is loaded into loading wells in the gel slab before the electric field is turned on. Then, an electric field is applied. The DNA molecules move in the opposite direction of the electric field because they are negatively charged. As the electric field is applied, DNA molecules travel at different speeds according to their sizes, but the directions in which they migrate are always the same. Eventually, sample DNA molecules are separated into different bands, each of which contains DNA molecules of the same size, as shown in FIG. 1. Shorter DNA fragments move faster than longer ones. Therefore, they are separated according to their sizes. However, this standard method only works effectively for DNA molecules smaller than 40 kbp. Above this range, the standard method has to be modified. In particular, the applied electric field can no longer be DC, but is made to alternate between two different orientations. This modified scheme (pulsed-field gel electrophoresis) is routinely used in modern molecular biology laboratories, but it typically takes a few days to fractionate one set of DNA samples.

What is needed, and has not heretofore been provided, is a method and apparatus for quickly, or even continuously, fractionating charged macro-molecules.

OBJECTS AND SUMMARY OF THE INVENTION

It is an object of the present invention to provide a method and apparatus for quickly fractionating charged macro-molecules.

It is an additional object of the present invention to provide a method and apparatus for continuously fractionating charged macro-molecules.

It is a further object of the present invention to provide a method and apparatus for fractionating macro-molecules using asymmetric pulsed electrophoresis wherein an alternating electric field having two different orientations is applied, and one of the fields is stronger than the other in terms of duration or intensity, or the field is otherwise asymmetric.

The present invention relates to a method and apparatus for fractionation of charged macro-molecules such as DNA. DNA solution is loaded into a matrix including an array of obstacles. An alternating electric field having two different fields at different orientations is applied. The alternating electric field is asymmetric in that one field is stronger in duration or intensity than the other field, or is otherwise asymmetric. The DNA molecules are thereby fractionated according to size and are driven to a far side of the matrix where the fractionated DNA is recovered. The fractionating electric field can be used to load and recover the DNA to operate the process continuously.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

The present invention relates to a method and apparatus for fractionation of charged macro-molecules such as DNA. DNA solution is loaded into a matrix including an array of obstacles. An alternating electric field having two different fields at different orientations is applied. The alternating electric field is asymmetric in that one field is stronger in duration or intensity than the other field, or is otherwise asymmetric. The DNA molecules are thereby fractionated according to size and are driven to a far side of the matrix where the fractionated DNA is recovered. The fractionating electric field can be used to load and recover the DNA to operate the process continuously.

The present invention provides a method and apparatus for the fractionation of macromolecules on micro/nano-fabricated support materials (a.k.a. matrices). Because the motion of DNA molecules can be accurately controlled in micro/nano-fabricated environments, the fractionation of DNA can be achieved with very high resolution in a short time (i.e. seconds), even for DNA molecules larger than 100 kbp. In addition, the process can be operated continuously, i.e., DNA is loaded, fractionated, and recovered at the same time. Moreover, because this method exploits micro/nano-fabricated structure, it can be readily integrated into lab-on-a-chip devices as a component.

Figure 1:
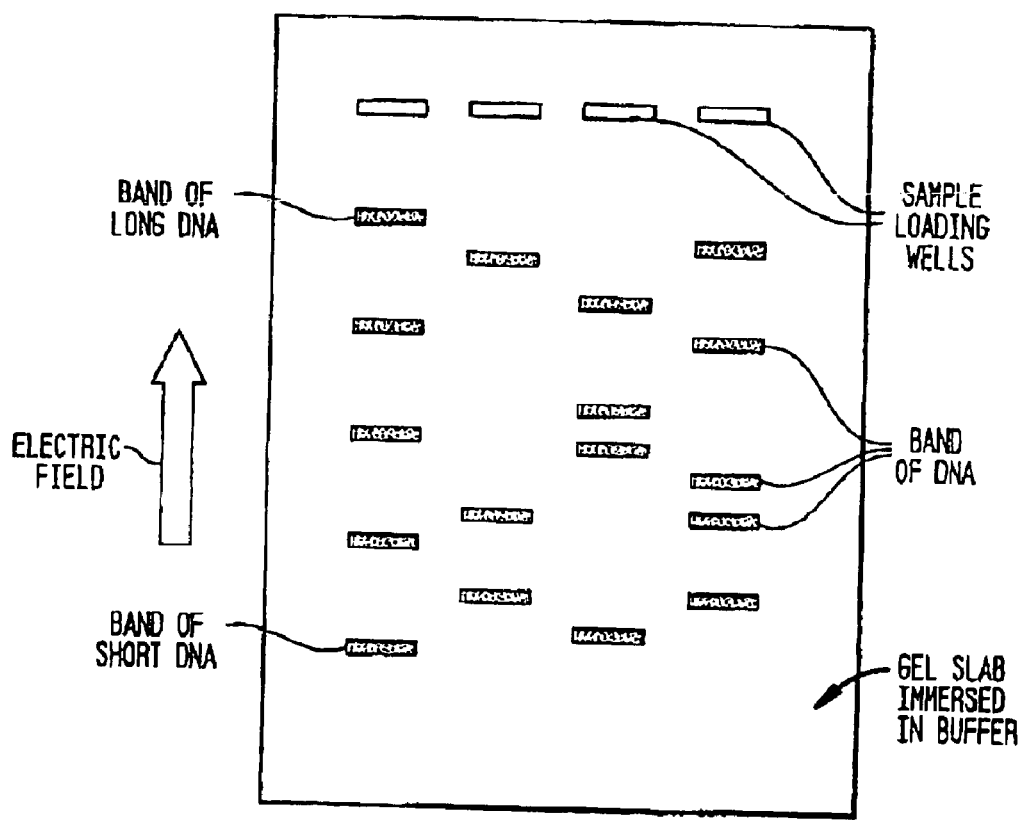
FIG. 1 shows conventional gel electrophoresis.
Figure 2:
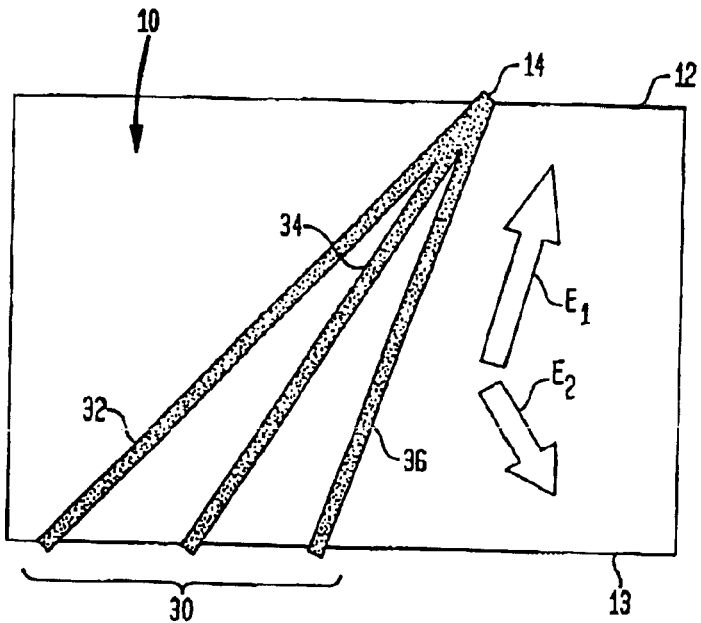
FIG. 2 is a diagram showing asymmetric pulsed-field electrophoresis in micro/nano-fabricated matrices according to the present invention.

According to the present invention, DNA molecules enter from one point or loading channel 14 on the boundary 12 of the matrix 10 as shown in FIG. 2. The molecules are subsequently fractionated into different bands at different orientations, according to their sizes, as they are driven towards the other side 13 of the matrix 10, where the purified DNA molecules 30 are finally recovered. The DNA molecules are fractionated into short fragments 32 at one end, long fragments 36 at the other end, and medium fragments 34 therebetween. The electric field ($E_1$ and $E_2$) that fractionates the DNA sample can also be used to load and recover the sample, enabling the process to be operated continuously.

A mixture of DNA molecules emerges continuously from the loading channel. The support material comprises a micro/nano-fabricated porous structure, in which DNA molecules can move. An alternating electric field, shown in $E_1$ and $E_2$, is applied across the whole matrix. $E_1$ and $E_2$ are at an angle with respect to each other, preferably an obtuse angle, and have different intensities and/or durations. Because DNA molecules are stretched and moving in a zigzag way under the alternating field, shorter fragments move at an angle to longer fragments.

Figure 3:
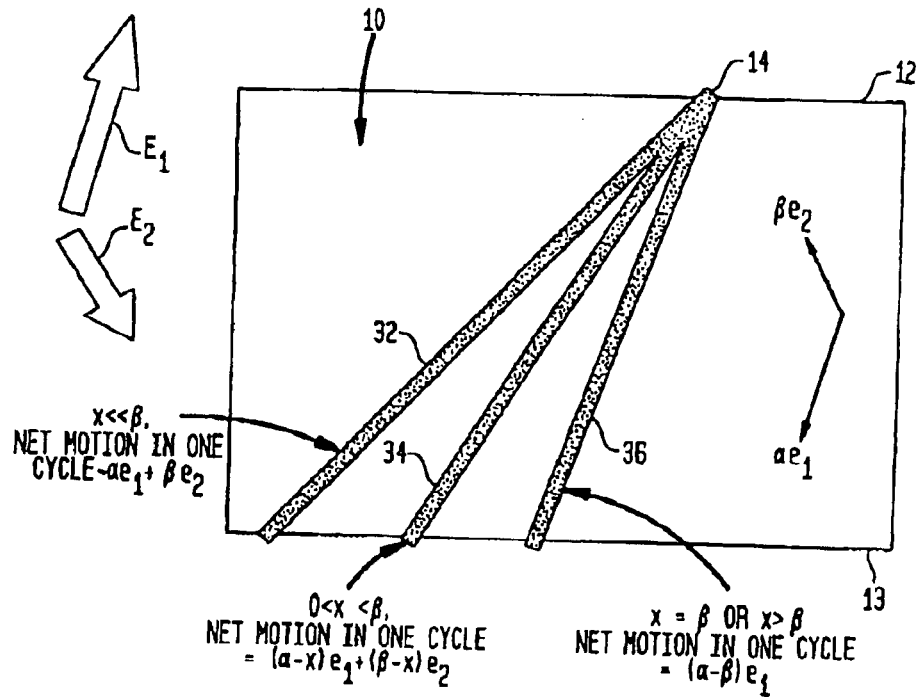
FIG. 3 is a diagram showing the basic principle of asymmetrical pulsed electrophoresis of the present invention.
Figure 4:
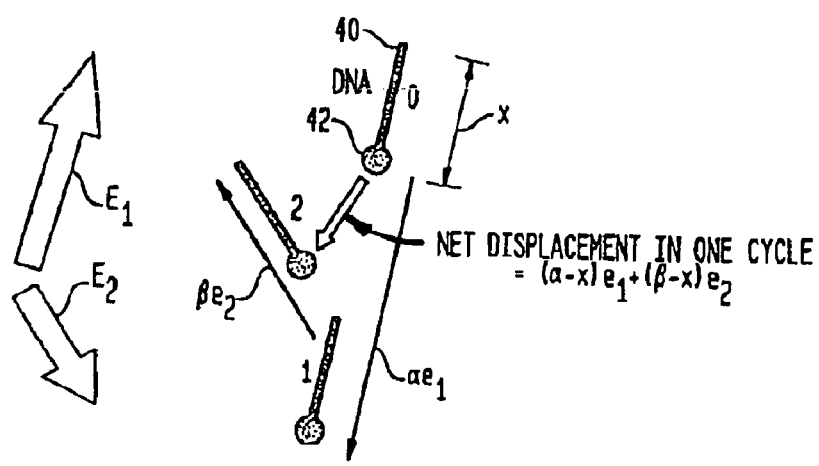
FIG. 4 shows the way stretched DNA molecules move under asymmetrical pulsed electric field.

When DNA molecules are subject to an alternating electric field between two orientations at an angle such as an obtuse angle, they are stretched to different lengths according to their molecular weight. Referring to FIG. 3, let the end-to-end length of a stretched DNA molecule be x. Assume that electric field $E_1$ displaces every DNA molecules by approximately the same displacement $\alpha$ $e_1$, whereas $E_2$ displaces every DNA molecules by approximately $\beta$ $e_2$ ($e_1$ and $e_2$ are unit vectors, and both $\alpha$ and $\beta$ are positive numbers, since DNA molecules are negatively charged and move opposite to an applied electric field). This is a valid assumption because it is known that all DNA molecules have virtually the same mobility due to the fact that the long range hydrodynamic interaction is shielded by the counter ion layers. For the simplicity, let $\alpha$ be larger than $\beta$. This can be achieved by pulsing along $-e_1$ longer than along $-e_2$, and/or by making the electric field stronger along $-e_1$ than along $-e_2$. Because the electric field is alternating between two different directions, the DNA molecules will move in a zigzag way. Ideally, the electric field is chosen so that $x<\beta<\alpha$. The net motion of very short DNA molecules ($x<<\beta$) in one pulsing cycle (a cycle refers to applying $E_1$, then $E_2$) is simply $\alpha$ $e_1+\beta$ $e_2$. On the contrary, very long molecules ($x>\beta$) travel ($\alpha-\beta$) $e_1$ in a cycle. Even though this could be rather surprising at first glance, it is not hard to understand if it is realized that when the field is switched from one to the other, the tails 40 of DNA strands become the ends that lead the motion and the heads 42 follow, as shown in FIG. 4. In principle, we can predict the angles of the bands into which DNA mixtures are fractionated by this technique, if the stretched lengths of DNA molecules are smaller than or equal to $\beta$. Within this range ($x<\beta$ or $x=\beta$), the net motion of DNA molecules in one cycle is ($\alpha-x$) $e_1+(\beta-x)$ $e_2$. Purified DNA molecules can be recovered at the bottom of the support material, after many cycles. In one cycle, a DNA molecule stretched to length x will travel ($\alpha-x$) $e_1+(\beta-x)$ $e_2$.

As shown in FIG. 4, an alternating electric field not only stretches DNA molecules to a linear conformation, but also makes them to move in a zigzag way. The initial position of a DNA molecule is labeled as 0. The big dot on one end of the DNA represents the "head" 42 of the molecule. The other end of the molecule is referred to as the "tail" 40. When $E_1$ is applied, the DNA molecule moves to position 1. The tail 40 leads the motion as the electric field is switched to $E_2$. By the end of one cycle, the molecule moves to position 2, and the net displacement in one cycle ($\alpha-x$) $e_1+(\beta-x)$ $e_2$.

By electric field, what is meant is the spatial average of the field around a location over a length scale of several obstacles, not the microscopic field distribution around a single obstacle. Any electric field at a given location, whose direction varys with time, can be resolved uniquely into two sequences of electric pulses according to the instantaneous direction of the field. The first sequence of electric pulses comprises the electric field pointing to one side of the average field vector over the whole period of time when the field is applied to fractionate the molecules. The second sequence of electric pulses comprises the electric field pointing to the other side of the average field vector. If the field vector at a moment is at the same direction or at the opposite direction of the average field vector, it is excluded in either of the pulse sequence. By asymmetrical electric field, what is meant is that the two sequences of electric pulses, resolved from a given electric field, as a function of time, have vector integrals over time that is not symmetric about the time-averaged field direction. Said another way, the electric fields, fields $\vec{E}(t)$ whose odd-order integrals over time, $\int |\vec{E}(t)|^n \vec{E}(t)dt$, are not at the time-average field orientation for every n, where n is any positive even integer. As such, by applying electric fields with different orientations and different strengths, i.e. different durations or different intensities or both, one applies an asymmetric field. Asymmetric fields can also be generated by sweeping signals in terms of orientation, duration and intensity. In the past, the field has first and second pulse sequences whose vector integrals over time are symmetrical about the average field.

Experimental Results

Figure 5:
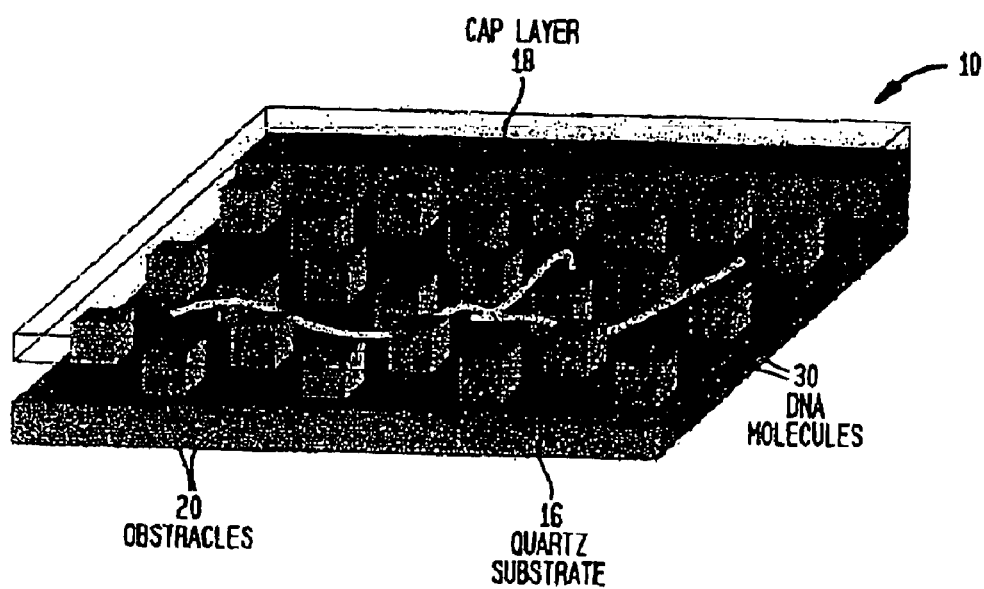
FIG. 5 shows a support material (matrix) for use in fractionation of DNA according to the present invention.
Figure 6A:
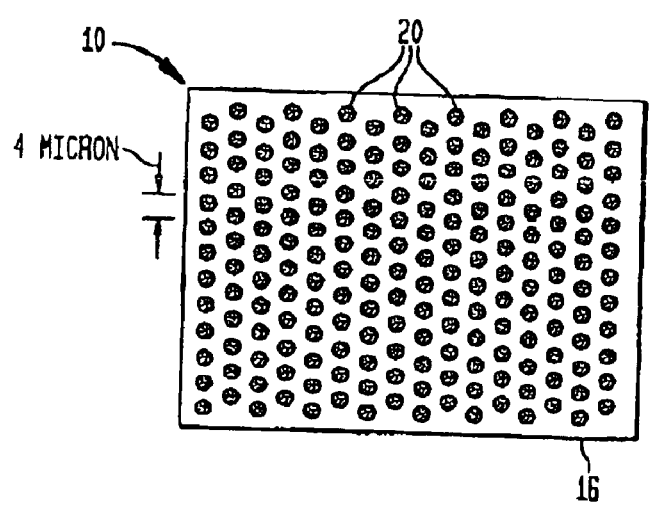
FIG. 6A is a top view and FIG. 6B is a side view of the microfabricated support material shown in FIG. 5.
Figure 6B:
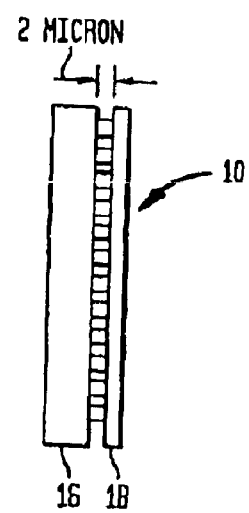
Figure 7:
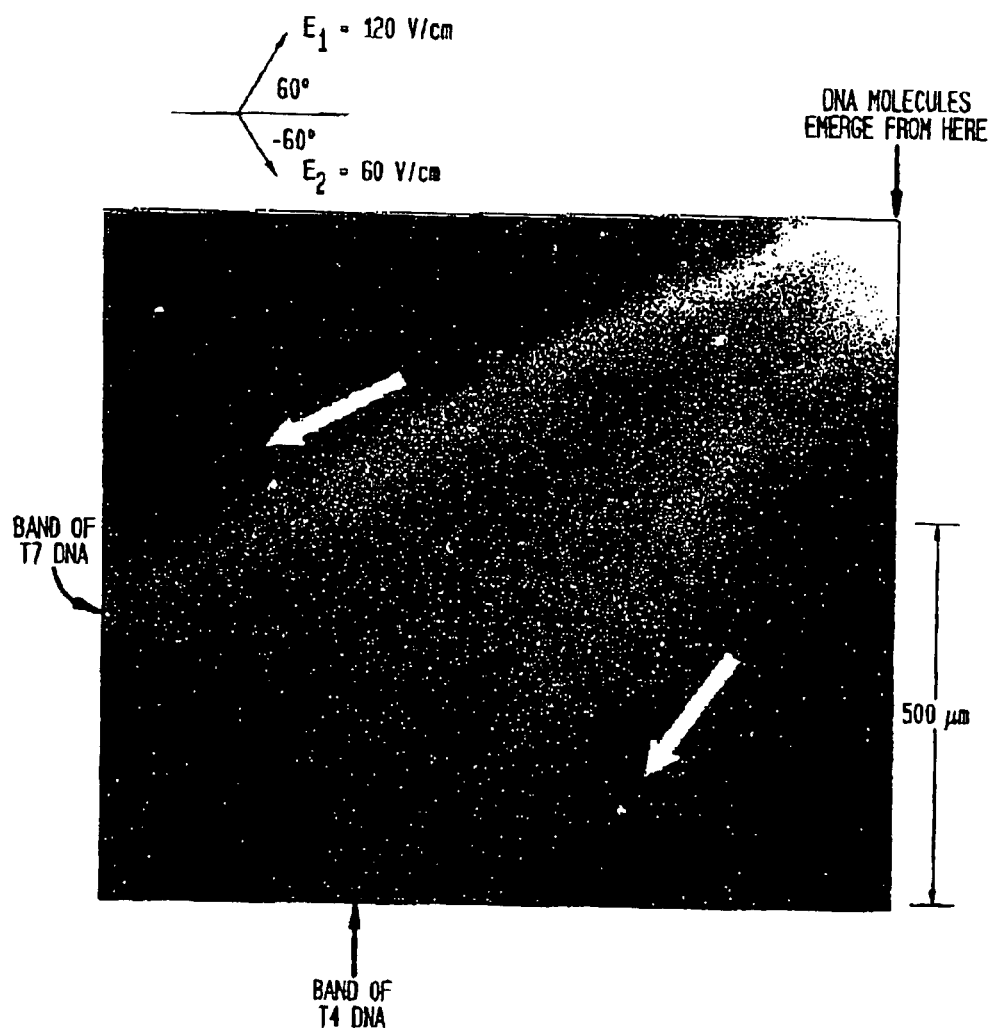
FIG. 7 shows fractionation of T4 and T7 DNA.

The following example uses a microfabricated matrix 10. As shown in FIG. 5, the matrix 10 consists of two parts: a microfabricated array of obstacles 20 in quartz, and a cap layer 18 that is hermetically bonded to the microfabricated side of the quartz substrate 16. The quartz substrate 16 is surface-micromachined using standard microfabrication techniques. The substrate is subsequently bonded to a glass cap layer 18 hermetically. The cavities between the substrate and the cap layer become microfluidic channels in which DNA molecules are fractionated. The dimensions of this microfabricated device are depicted in FIGS. 6a and 6b. FIG. 6a is the top view of the matrix 10, and FIG. 6b is a side view of the matrix 10. The matrix 10 in this case is a hexagonal array of obstacles 20. Each obstacle 20 comprises a cylindrical post 2 μm in diameter. The center-to-center distance between neighboring obstacles is 4 μm. The uniformity of the electric field across the whole matrix is controlled accurately by the peripheral structures surrounding the matrix. FIG. 7 shows the fractionation of T4 (169 kbp) and T7 (40 kbp) DNA molecules. The pulse condition is $E_1$=120 V/cm at 60° with respect to the horizontal boundary, and $E_2$=60 V/cm at −60°. The DNA injected into the matrix is 10 μg/ml of T4 DNA and 10 μg/ml of T7 DNA in ½ TBE buffer. The duration of $E_1$ is identical to that of $E_2$, which is 166 msec. The frequency at which the electric field alternates is 3 Hz. Clearly, the DNA mixture separates into two bands.

Having thus described the invention in detail, it is to be understood that the foregoing description is not intended to limit the spirit and scope thereof. What is desired to be protected by Letters Patent is set forth in the appended claims.

What is claimed is:

1. A method of continuously fractionating charged macromolecules comprising:

loading molecules into a matrix of obstacles;

applying an asymmetric electric field to the matrix to separate the molecules according to size along a horizontal direction of the matrix; and collecting separated molecules at a plurality of locations along a bottom edge of the matrix, wherein the step of applying an asymmetric electric field to the matrix comprises applying an electric field which is alternating in direction as a function of time at a location in the matrix, and which has a time average of an electric field vector over many cycles, whereby the time integral of the vector at the same location over a part of the cycles when the electric field is instantaneously pointing to one side of the vector is not spatially symmetric about the vector with the time integral of the vector over another part of the cycles at the same location when the electric field is instantaneously pointing to another side of the vector.

2. The method of claim 1, wherein the step of applying an asymmetric electric field to the matrix comprises applying to the matrix time-dependent electric fields $\vec{E}(t)$ whose odd-order integrals over time, $\int |\vec{E}(t)|^n \vec{E}(t)dt$, are not at the time-average field orientation for every n, where n is any positive even integer.

3. The method of claim 1, wherein the step of applying an asymmetric electric field comprises:

alternating first and second electric pulses of first and second waveforms;

maintaining the integral of one of the first or second pulses' amplitude over time larger than that of the other pulse;

varying the orientation of the first electric pulse within first and second orientations, and the orientation of the second electric pulse within third and forth orientations.

4. The method of claim 3, wherein the first and second waveforms are square pulses.

5. The method of claim 4, wherein one of the square pulses is of higher amplitude than the other.

6. The method of claim 4, wherein one of the square pulses is of longer duration than the other.

7. The method of claim 1, wherein the step of applying an asymmetric electric field comprises:

alternating first and second electric pulses of first and second waveforms;

maintaining the integral over time of one of the first or second pulses' amplitudes larger than that of the other pulse; and applying the first and second electric pulses at first and second fixed orientations.

8. The method of claim 7, wherein the first and second waveforms are square pulses.

9. The method of claim 8 wherein one of the square pulses is of higher amplitude than the other.

10. The method of claim 8, wherein one of the square pulses is of longer duration than the other.

11. The method of claim 1, wherein the charged macro-molecules are deoxyribonucleic acid (DNA).

12. The method of claim 1, wherein the molecules are loaded using electric fields.

13. The method of claim 1, wherein the molecules are extracted from the array of obstacles using electric fields.

14. The method of claim 1, wherein the molecules are routed to the next processing step after fractionation.

15. A method of continuously fractionating charged macro-molecules comprising:

loading molecules into a matrix of obstacles;

applying an asymmetric electric field to the matrix to separate the molecules according to size along a horizontal direction of the matrix; and collecting separated molecules at a plurality of locations along a bottom edge of the matrix, wherein the step of applying an asymmetric electric field to the matrix comprises applying to the matrix time-dependent electric fields $\vec{E}(t)$ whose odd-order integrals over time, $\int |\vec{E}(t)|^n \vec{E}(t)dt$, are not at the time-average field orientation for every n, where n is any positive even integer.

16. The method of claim 15, wherein the step of applying an asymmetric electric field comprises:

alternating first and second electric pulses of first and second waveforms;

maintaining the integral of one of the first or second pulses' amplitude over time larger than that of the other pulse;

varying the orientation of the first electric pulse within first and second orientations, and the orientation of the second electric pulse within third and forth orientations.

17. The method of claim 16, wherein the first and second waveforms are square pulses.

18. The method of claim 17, wherein one of the square pulses is of higher amplitude than the other.

19. The method of claim 17, wherein one of the square pulses is of longer duration than the other.

20. The method of claim 15, wherein the step of applying an asymmetric electric field comprises:

alternating first and second electric pulses of first and second waveforms;

maintaining the integral over time of one of the first or second pulses' amplitudes larger than that of the other pulse; and applying the first and second electric pulses at first and second fixed orientations.

21. The method of claim 20, wherein the first and second waveforms are square pulses.

22. The method of claim 21, wherein one of the square pulses is of higher amplitude than the other.

23. The method of claim 21, wherein one of the square pulses is of longer duration than the other.

24. The method of claim 15, wherein the charged macro-molecules are deoxyribonucleic acid (DNA).

25. The method of claim 15, wherein the molecules are loaded using electric fields.

26. The method of claim 15, wherein the molecules are extracted from the array of obstacles using electric fields.

27. The method of claim 15, wherein the molecules are routed to the next processing step alter fractionation.

28. A method of continuously fractionating charged macro-molecules comprising:

loading molecules into a matrix of obstacles;

applying an asymmetric electric field to the matrix to separate the molecules according to size along a horizontal direction of the matrix; and collecting separated molecules at a plurality of locations along a bottom edge of the matrix, wherein the step of applying an asymmetric electric field comprises:

alternating first and second electric pulses of first and second waveforms;

maintaining the integral over time of one of the first or second pulses' amplitudes larger than that of the other pulse; and applying the first and second electric pulses at first and second fixed orientations.

29. The method of claim 28, wherein the step of applying an asymmetric electric field comprises:
   alternating first and second electric pulses of first and second waveforms;
   maintaining the integral of one of the first or second pulses' amplitude over time larger than that of the other pulse;
   varying the orientation of the first electric pulse within first and second orientations, and the orientation of the second electric pulse within third and forth orientations.

30. The method of claim 29, wherein the first and second waveforms are square pulses.

31. The method of claim 30, wherein one of the square pulses is of higher amplitude than the other.

32. The method of claim 30, wherein one of the square pulses is of longer duration than the other.

33. The method of claim 28, wherein the first and second waveforms are square pulses.

34. The method of claim 33, wherein one of the square pulses is of higher amplitude than the other.

35. The method of claim 33, wherein one of the square pulses is of longer duration than the other.

36. The method of claim 28, wherein the charged macro-molecules are deoxyribonucleic acid (DNA).

37. The method of claim 28, wherein the molecules are loaded using electric fields.

38. The method of claim 28, wherein the molecules are extracted from the array of obstacles using electric fields.

39. The method of claim 28, wherein the molecules are routed to the next processing step after fractionation.

40. A method of continuously fractionating charged macro-molecules comprising:
   loading molecules into a matrix with an array of obstacles;
   applying to the matrix electric fields whose amplitudes are constant in time;
   varying field orientations of the electric fields with time to create an asymmetrical electric field to separate the molecules according to size along a horizontal direction of the matrix; and
   collecting separated molecules at a plurality of locations along a bottom edge of the matrix,
   wherein the step of varying the field orientation with time to create an asymmetrical electric field comprises varying the field orientation with time in such a manner that $\int [\theta(t)]^{n+1} dt$ are not zero for every n, where $\theta(t)$ is field orientation with respect to the time-average field orientation, and n is any even integer larger than zero.

41. The method of claim 40, wherein the fields alternate between two fixed orientations.

42. The method of claim 40, wherein the charged macro-molecules are deoxyribonucleic acid (DNA).

43. The method of claim 40, wherein the molecules are loaded using electric fields.

44. The method of claim 40, wherein the molecules are extracted from the array of obstacles using electric fields.

45. The method of claim 40, wherein the molecules are routed to the next processing step after fractionation.

* * * * *

UNITED STATES PATENT AND TRADEMARK OFFICE
CERTIFICATE OF CORRECTION

| | | |
|---|---|---|
| PATENT NO. | : 6,881,317 B2 | Page 1 of 1 |
| APPLICATION NO. | : 10/022189 | |
| DATED | : April 19, 2005 | |
| INVENTOR(S) | : Lotien Richard Huang et al. | |

It is certified that error appears in the above-identified patent and that said Letters Patent is hereby corrected as shown below:

On the Title page, Item (56) References Cited, Other pubs please add the following reference:

Huang, et al., "Generation of Large-Area Tunable Uniform Electric Fields in Microfluidic Arrays for Rapid DNA Separation," Technical Digest of the International Electron Devices Meting, pp. 363-366 (2001).

Signed and Sealed this

Eleventh Day of July, 2006

JON W. DUDAS
*Director of the United States Patent and Trademark Office*